United States Patent [19]

Ames-Ooten et al.

[11] Patent Number: 5,575,784
[45] Date of Patent: Nov. 19, 1996

[54] DISPOSABLE TRAINING PANT WITH IMPROVED DISPOSAL MEANS

[75] Inventors: Kathleen Q. Ames-Ooten, Cincinnati; Donald C. Roe, West Chester, both of Ohio

[73] Assignee: The Procter & Gamble Company, Cincinnati, Ohio

[21] Appl. No.: 552,178

[22] Filed: Nov. 2, 1995

[51] Int. Cl.⁶ .................................................. A61F 13/15
[52] U.S. Cl. .................................. 604/385.1; 604/389
[58] Field of Search ................... 604/389–391, 604/385.1

[56] References Cited

U.S. PATENT DOCUMENTS

| | | | |
|---|---|---|---|
| 3,620,217 | 11/1971 | Gellert | 128/284 |
| 3,930,501 | 1/1976 | Schaar | 128/287 |
| 4,493,713 | 1/1985 | Izzo | 604/385 |
| 4,604,096 | 8/1986 | Dean et al. | 604/385 A |
| 4,787,897 | 11/1988 | Torimae et al. | 604/389 |
| 4,869,724 | 9/1989 | Scripps | 604/389 |
| 4,923,455 | 5/1990 | Dean et al. | 604/389 |
| 4,963,140 | 10/1990 | Robertson et al. | 604/389 |
| 5,176,671 | 1/1993 | Roessler et al. | 604/391 |
| 5,246,433 | 9/1993 | Hasse et al. | 604/396 |
| 5,279,604 | 1/1994 | Robertson et al. | 604/389 |
| 5,403,302 | 4/1995 | Roessler et al. | 604/391 |

FOREIGN PATENT DOCUMENTS 6-77718 11/1994 Japan ........................... A61F 13/15

Primary Examiner—Robert A. H. Clarke
Attorney, Agent, or Firm—Kevin C. Johnson; Steven W. Miller; Jacobus C. Rasser

[57] ABSTRACT

A disposable garment having an improved disposal means so as to provide convenient disposal of the disposable garment. The disposable garment includes a chassis having a front portion, a rear portion, and a crotch portion positioned between the front portion and the rear portion. Seams join the front and rear portions together to form two leg openings and a waist opening. The improved disposal means is preferably joined to the outer layer of the disposable garment and includes a frangible section to provide for separation of the disposal means into independent portions.

13 Claims, 4 Drawing Sheets

DISPOSABLE TRAINING PANT WITH IMPROVED DISPOSAL MEANS

FIELD OF THE INVENTION

The present invention relates to disposable garments having fixed sides, which are placed in position on the wearer by inserting the wearer's legs into the leg openings and sliding the disposable garment into position about the wearer's lower torso. Examples of such disposable garments would include disposable underwear for children (e.g., toddlers) or adults, and disposable panties which may be used with catamenial devices such as tampons or sanitary napkins. The present invention relates more particularly to disposable absorbent articles such as training pants, incontinent garments (parities or briefs), and the like, having an improved disposal means that provides for convenient disposal.

BACKGROUND OF THE INVENTION

Infants and other incontinent individuals wear disposable absorbent articles to receive and contain urine and other bodily exudates. Absorbent articles having fixed sides, e.g. disposable training pants, have been popular for use on toilet-training children. An example of a disposable training pant is described in U.S. Pat. No. 5,246,433 issued to Hasse et al. on Sep. 21, 1993.

The use of adhesive disposal systems for securing a training pant in a configuration for disposal is well known in the art. While prior art adhesive disposal systems are fairly effective in securing a training pant in a configuration for disposal, they do have shortcomings. One shortcoming is that they do not effectively seal the training pant to contain the contents within the soiled training pant. Prior art adhesive disposal systems have only one member positioned on the outer cover of the training pant that effectively keeps the training pant in a rolled-up configuration but does not effectively seal the leg openings to contain the contents within the soiled training pant.

It is therefore, an object of the present invention to provide a disposable garment with a disposal means that will effectively contain the contents within the soiled training pant.

SUMMARY OF THE INVENTION

The present invention provides a disposable garment such as a disposable training pant, comprising a chassis having a front portion, a rear portion opposed to the front portion, and a crotch portion positioned between the front portion and the rear portion. The chassis comprises an inner layer and an outer layer. Seams join the front portion to the rear portion so as to form an elasticized waist opening and two elasticized leg openings. Disposal means is joined to the outer layer for allowing the disposable garment to be secured in a configuration that provides convenient disposal of the disposable garment. The disposal means comprises a frangible section to provide for separation of the disposal means into independent portions. The disposable garment additionally comprises an absorbent assembly comprising a backsheet, a topsheet, and an absorbent core positioned between the topsheet and the backsheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
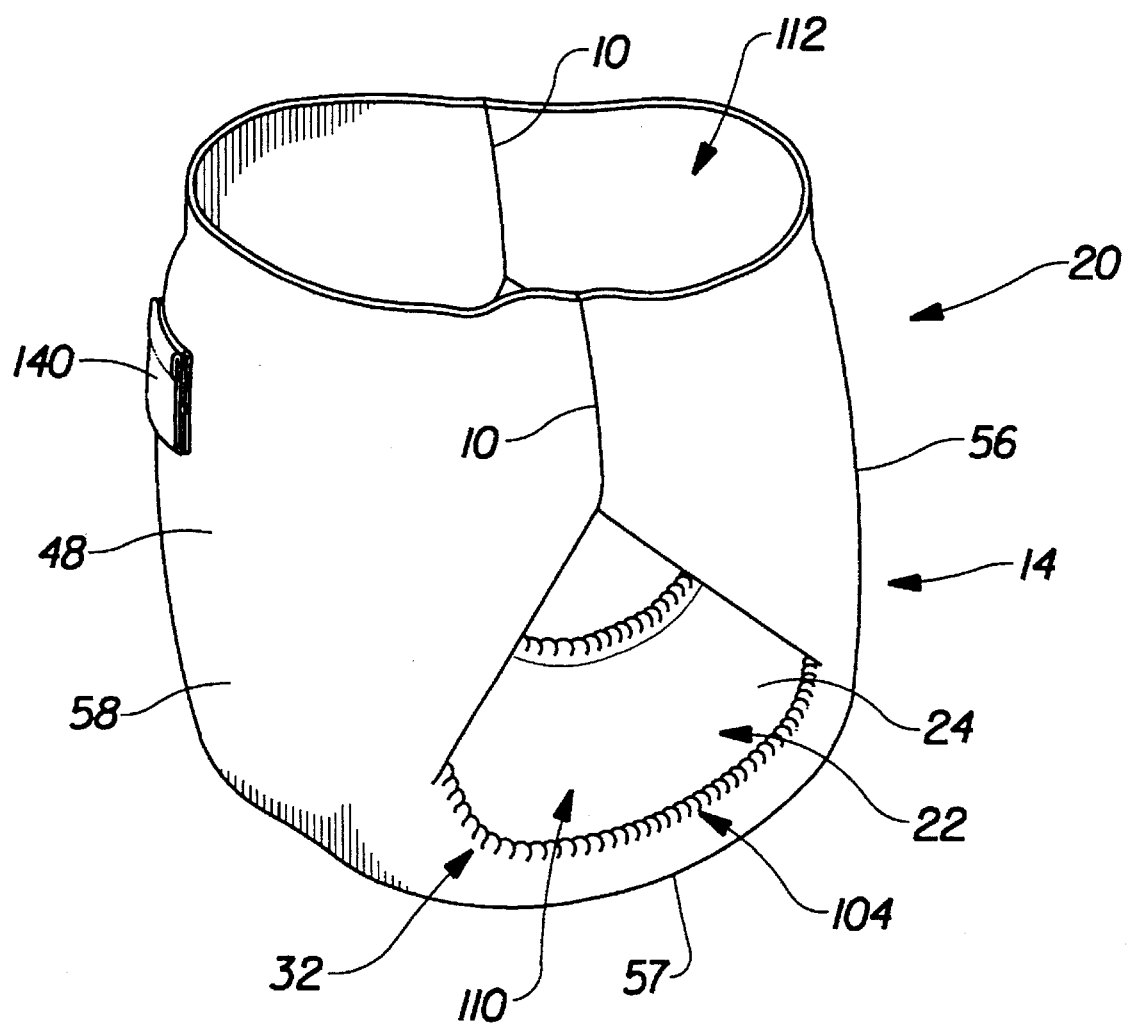
FIG. 1 is a perspective view of the disposable training pant embodiment of the present invention in a typical in-use configuration as it would be applied to a wearer.

A unitary disposable garment is one which is intended to be discarded after it is used (i.e., it is not intended to be laundered or otherwise restored or reused), and which does not require separately manipulative parts such as a separate chassis and separate ear flaps. The disposable garment may be provided with an absorbent assembly which is placed in close proximity to the body of the wearer to absorb and contain the various exudates discharged from the body. A preferred embodiment of the unitary disposable garment of the present invention, disposable training pant 20, is shown in FIG. 1. The training pant 20 of FIG. 1, comprises a chassis 14, side seams 10, leg openings 110, a waist opening 112, an absorbent assembly 22, and a disposal means 140.

Figure 2:
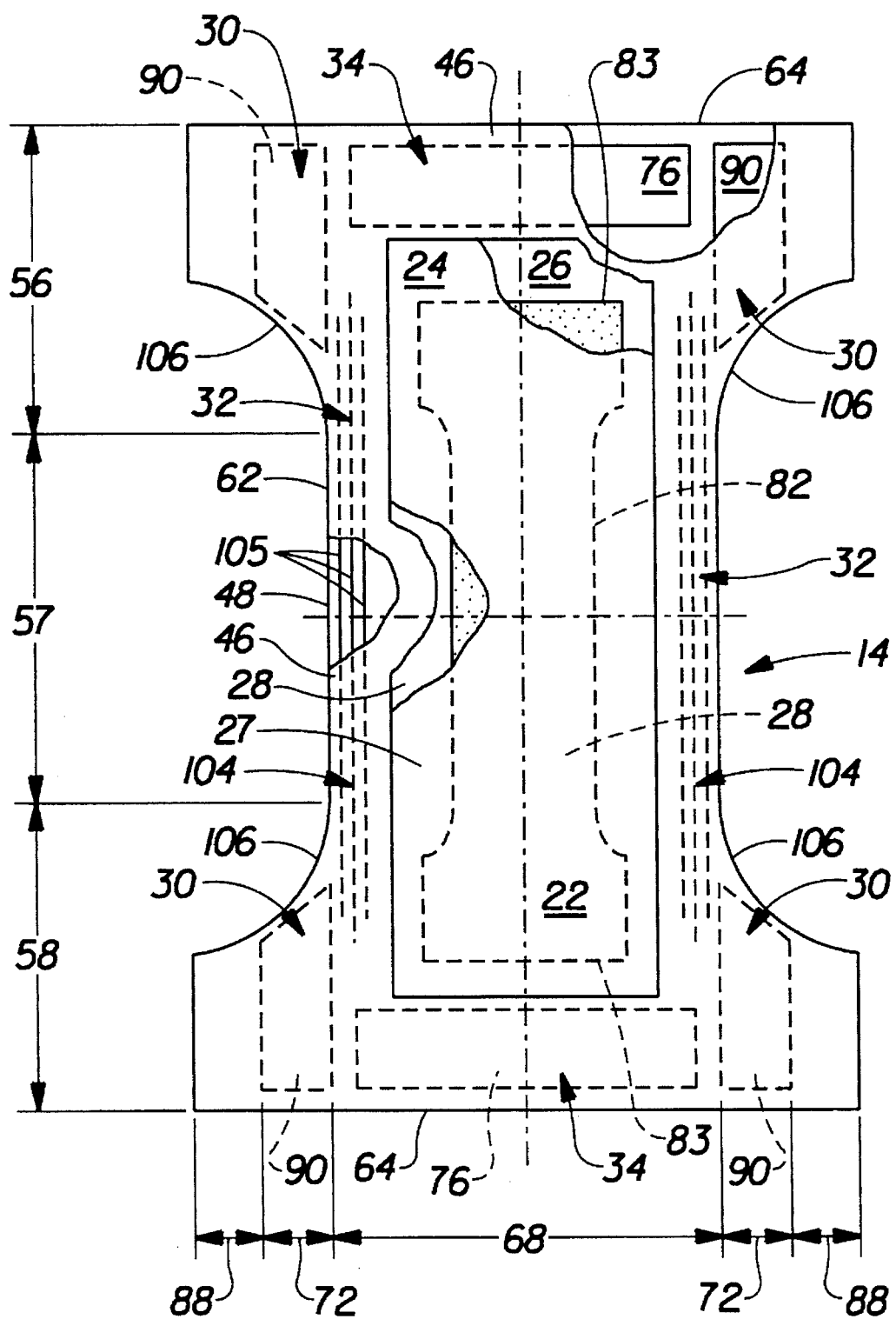
FIG. 2 is a plan view of the chassis of the disposable training pant embodiment of the present invention having portions cut away to reveal the underlying structure, the surface which will form the outer surface of the disposable garment facing away from the viewer.

FIG. 2 is a partially cut-away perspective view of the disposable training pant 20 of FIG. 1, prior to the front portion 56 and the rear portion 58 of the chassis 14 being joined together by the seams 10. The chassis 14 of the present invention preferably has a symmetric, modified hour-glass shape. The chassis 14 will have at least a front portion 56, a rear portion 58, a crotch portion 57, longitudinal side regions 88, and ear flaps 72 and will comprise an elastic ear flap member 90 operatively associated with each ear flap 72 to form a laminated ear flap. The absorbent assembly 22 is secured to the chassis 14.

As shown in FIG. 2, a preferred embodiment of the chassis 14 further comprises an outer layer 48 and an inner layer 46 with the elastic ear flap members 90, elastic waistband members 76, and elastic strands 105 preferably secured between the inner layer 46 and outer layer 48.

The outer layer 48 is that portion of the chassis 14 which will form the exterior of the disposable training pants 20, i.e., face away from the wearer. The outer layer 48 is compliant, soft feeling, and non-irritating to the wearer's skin. A suitable outer layer may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers.

Preferably, the outer layer 48 is hydrophobic and is made of a material containing a significant amount of thermoplastic fibers, typically 50% or more, preferably 100%. Preferably the outer layer is a carded nonwoven web of polypropylene fibers. A suitable outer layer is Series 6700 Nonwovens manufactured by Scott Nonwovens of Landisville, N.J.

The inner layer 46 is that portion of the chassis 14 which will form the interior of the chassis 14, and will contact at least the waist and legs of the wearer. The inner layer is also compliant, soft feeling, and non-irritating to the wearer's skin. A suitable inner layer 46 may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. Preferably the inner layer 46 is made of a material containing a significant amount of thermoplastic fibers, typically 50% or more, preferably 100%. Preferably the inner layer is also a carded nonwoven web of polypropylene fibers. More preferably, the inner layer 46 is made of the same material as the outer layer 48. A suitable inner layer is Series 6700 Nonwovens manufactured by Scott Nonwovens of Landisville, N.J.

The inner layer 46 is preferably positioned adjacent to the outer layer 48 and is preferably joined thereto by attachment means (not shown) such as those well known in the art. For example, the inner layer 46 may be secured to the outer layer 48 by a uniform continuous layer of adhesive, a patterned layer of adhesive, or an array of separate lines, spirals, or spots of adhesive. Adhesives which have been found to be satisfactory are manufactured by Findley Adhesives of Elm Grove, Wis. and marketed as Findley 2031. Alternatively, the attachment means may comprise heat bonds, pressure bonds, ultrasonic bonds, dynamic mechanical bonds, or any other suitable attachment means or combinations of these attachment means as are known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the inner layer 46 and the outer layer 48 are indirectly joined together by directly joining them to the elastic ear flap members 90, elastic waistband member 76, and elastic strands 105 and are joined directly to each other in the areas extending beyond the elastic ear flap members 90, elastic waistband members 76, and elastic strands 105.

In a preferred embodiment of the present invention, at least a portion of the chassis inner and outer covers 46, 48 will be subjected to mechanical stretching in order to provide a "zero strain" stretch laminate that forms the elasticized ear flaps 30. Thus, the inner and outer layers 46, 48 are preferably elongatable, most preferably drawable, but not necessarily elastomeric, so that the inner and outer layers 46, 48 will, upon mechanical stretching, be at least to a degree permanently elongated such that they will not fully return to their original undistorted configuration. In preferred embodiments, the inner and outer layers 46, 48 can be subjected to mechanical stretching without undue rupturing or tearing. Thus, it is preferred that the inner and outer covers 46, 48 have a low cross-machine direction (lateral direction) yield strength.

The chassis 14 of the disposable training pant 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 issued to Buell on Jan. 14, 1975, describes a disposable diaper which provides a contractible leg opening having a side flap and one or more elastic members to provide an elasticized leg cuff (gasketing cuff). U.S. Pat. No. 4,9089,803 issued to Aziz and Blaney on Mar. 20, 1990, describes a disposable diaper having "stand-up" elasticized flaps (barrier cuffs) to improve the containment of the leg regions. U.S. Pat. No. 4,695,278 issued to Lawson on Sep. 22, 1987, describes a disposable diaper having dual cuffs including a gasketing cuff and a barrier cuff. U.S. Pat. No. 4,704,115 issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least a side flap 104 and one or more elastic strands 105.

The chassis 14 of the disposable training pant 20 further preferably comprises an elasticized waistband 34 disposed adjacent the end edge 64 of the disposable training pant 20 in at least the rear portion 58, and more preferably has an elasticized waistband 34 disposed in both the front portion 56 and the rear portion 58. The waistband of the disposable training pant 20 is that portion which is intended to be placed adjacent the wearer's waist. The elasticized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable training pant 20 extending from the end edge 64 of the disposable training pant 20 to at least the waist edge 83 of the absorbent core 28. While the elasticized waistband 34 can comprise a separate element affixed to the chassis 14 of the disposable training pant 20, the waistband is preferably an extension of other elements of the disposable training pant 20 such as the inner layer 46, the outer layer 48, or any combination of these elements and an elastomeric material joined thereto. Alternatively, the topsheet 24 and the backsheet 26 of the absorbent assembly 22, may extend beyond the edges of the absorbent core 28 and have an elastomeric material joined thereto to form an elasticized waistband. Disposable training-pants are often constructed so as to have two elasticized waistbands; one positioned in the front portion 56 and one positioned in the rear portion 58. The disposable training pant 20 at least has an elasticized waistband 34 disposed in at least the central region 68 of the rear portion 58. Preferably, as shown in FIG. 2, another elasticized waistband is disposed in the front portion 56. Preferably both elasticized waistbands 34 are disposed between the elasticized ear flaps 30.

The elasticized waistband 34 may be constructed in a number of different configurations including those described herein with regard to the elasticized side panels. In a preferred embodiment of the present invention shown in FIG. 2, the elasticized waistband 34 comprises an elastic waistband member 76 interposed between the inner cover 46 and the outer cover 48 and operatively associated with either or both the inner cover 46 and the outer cover 48 to gather the front portion 56 and rear portion 58 of the disposable training pant 20. An example of such an elasticized waistband for use herein is the elasticized waistband disclosed in U.S. Pat. No. 4,515,595 which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates or mechanically stretched pretensioned stretch laminates; and elastic strands made from rubber, LYCRA, or other materials. In a preferred embodiment, the elastic waistband member 76 comprises a heat shrinkable elastomeric film.

In an alternative embodiment, the elasticized waistbands 34 and the elasticized ear flaps 30 can be formed by securing a single piece of elastomeric material to the disposable garment 20 in both the ear flaps 72 and central region 68 of the front portion 56. Thus, the elasticized waistband 34 and the elasticized ear flaps 30 can be formed from the same piece of material to form a unitary structure.

In a preferred embodiment, the chassis 14 comprises elasticized ear flaps 30 in the front portion 56 and rear portion 58. The elasticized ear flaps 30 are unitary elements of the chassis, i.e. they are not separately manipulative elements secured to the chassis, but rather are formed from and are extensions of the chassis materials. The elasticized ear flaps 30 provide an elastically extensible feature that provides a more comfortable and contouring fit by initially conformably fitting the disposable garment to the wearer and sustaining this fit throughout the time of wear well past when the disposable garment has been loaded with exudates since the elasticized ear flaps allow the sides of the disposable garment to expand and contract.

As shown in FIG. 2, each ear flap 72 comprises that portion of the chassis 14 that extends laterally outwardly from and along the central region 68 of the chassis 14 to the longitudinal side region 88 of the chassis 14. The ear flap 72 generally extends longitudinally from the end edge 64 of the chassis 14 to the portions of the longitudinal edge 62 of the chassis 14 that forms the leg opening (this segment of the longitudinal edge 62 being designated as leg edge 106). In a preferred embodiment of the present invention, each ear flap is formed by the portions of the inner layer 46 and the outer layer 48 that extend beyond the central region 68 of the chassis 14.

In a preferred embodiment of the present invention, the elastic ear flap members 90 are operatively associated with the chassis 14 in the ear flaps 72, preferably between the inner layer 46 and the outer layer 48, so that the elastic ear flap members 90 allow the elasticized ear flaps 30 to be elastically extensible in the lateral direction (laterally elastically extensible). As used herein, the term "elastically extensible" means a segment or portion of the chassis that will elongate in at least one direction (preferably the lateral direction for the ear flaps and the waistbands) when tensional forces (typically lateral tensional forces for the ear flaps and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e., a "snappy" elastic).

In an especially preferred embodiment, the elastic ear flap member 90 is operatively associated in the ear flap 72 by joining the elastic ear flap member 90 to the inner layer 46, outer layer 48, or both while the elastic ear flap member 90 is in a substantially untensioned condition. At least a portion of the resultant composite elastomeric laminate containing the elastic ear flap member 90 is then subjected to mechanical stretching sufficient to permanently elongate the inner layer and the outer layer components (nonelastic components) of the laminate. The composite elastomeric laminate is then allowed to return to its substantially untensioned condition. The elasticized ear flap is thus formed into a "zero strain" stretch laminate. (Alternatively, the elastic ear flap member could be operatively associated in a tensioned condition and then subjected to mechanical stretching; although this is not a preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically extensible, at least up to the point of initial stretching, in the direction of initial stretching. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference.

Particularly preferred methods and apparatus used for making "zero strain" stretch laminates out of the inner layer, outer layer, and an elastomeric member positioned between the same, use meshing corrugated rolls to mechanically stretch the components. A discussion of suitable apparatus and methods for mechanically stretching portions of a diaper is contained in the hereinbefore referenced U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in U.S. Pat. No. 5,167,897 issued to Gerald M. Weber et al. on Dec. 1, 1992; U.S. Pat. No. 5,156,793 issued to Kenneth B. Buell et al. on Oct. 20, 1992; and U.S. Pat. No. 5,143,679 issued to Gerald M. Weber et al. on Sep. 1, 1992; each of which are incorporated herein by reference.

In a preferred embodiment of the chassis as shown in FIG. 2, the longitudinal side region 88 is that portion of the chassis 14 that extends laterally outwardly from the ear flap 72 to the longitudinal edge 62 of the chassis 14. The longitudinal side region 88 generally extends longitudinally from the end edge 64 of the chassis 14 to the portion of the longitudinal edge 62 of the chassis 14 that forms the leg opening (this segment of the longitudinal edge 62 being designated as leg edge 106). While the longitudinal side region 88 can comprise a separate element affixed to the ear flap 72 of the chassis 14, the longitudinal side region is preferably an extension of other elements of the chassis 14 such as the inner layer 46, the outer layer 48, the topsheet 24 or the backsheet 26 or any combination of these elements. In a preferred embodiment of the present invention each longitudinal side region 88 is formed by portions of the inner layer 46 and outer layer 48 that extend beyond the ear flap 72.

Referring again to FIG. 1, seams 10 are preferably formed by bonding together the longitudinal side regions 88 of the front portion 56 with the longitudinal side regions 88 of the rear portion 58. The seam 10 can be formed in a number of different ways. For example the seam 10 can be formed by bonding together portions of outwardly extending longitudinal side regions 88 to form an outwardly extending fin seam, bonding together portions of inwardly extending longitudinal side regions 88 to form an inwardly extending fin seam, the longitudinal side regions 88 may be bonded together using any other seam configurations that are well known in the art. The bonding can be by any suitable means well known in the art appropriate for the specific material employed in the longitudinal side region 88 of the chassis 14; thus sonic sealing, heat sealing, adhesive bonding, sewing, and the like may be appropriate techniques. Examples of suitable seaming techniques are disclosed in U.S. Pat. No. 4,355,425 issued to Jones, et al. on Oct. 26, 1982; U.S. Pat. No. 4,619,649 issued to Roberts on Oct. 28, 1986; U.S. Pat. No. 4,909,804 issued to Douglas, Sr. on Mar. 20, 1990; and U.S. Pat. No. 5,246,433 issued to Hasse et al. on Sep. 21, 1993.

The training pant 20 will also comprise an absorbent assembly 22. The absorbent assembly 22 of the disposable training pant 20 is an insert, i.e. an element formed separately from the chassis and inserted therein. The absorbent assembly 22 is any absorbent means which is generally compressible, conformable, non-irritating to the wearer's skin, and capable of absorbing and retaining liquids such as urine and other certain body exudates.

As shown in FIG. 2, the absorbent assembly 22 of the disposable training pant 20 preferably comprises an absorbent core 28 and an outer covering layer comprising a topsheet 24 and a backsheet 26. The absorbent assembly 22 is preferably positioned adjacent the inner layer 46 and is preferably joined thereto by attachment means (not shown) such as those well known in the art. Suitable attachment means are described hereinbelow with respect to joining the backsheet 26 to the absorbent core 28.

The absorbent core 28 may be any absorbent means which is generally compressible, conformable, non-irritating to the wearer's skin, and capable of absorbing and retaining liquids such as urine and other certain body exudates. The absorbent core 28 has a garment surface 100, a body surface 101, side edges 82 and end edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable training pant 20. Further, the size and absorbent capacity of the absorbent core 28 may be varied to accommodate wearers ranging from infants through adults.

A preferred embodiment of the absorbent assembly 22 has a symmetric, modified hour-glass shape absorbent core 28. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic radiant, or may or may not contain absorbent gelling materials). An exemplary absorbent structure for use as the absorbent core 28 of the present invention that has achieved wide acceptance and commercial success is described in U.S. Pat. No. 4,610,678 issued to Weisman and Goldman on Sep. 9, 1986. U.S. Pat. No. 4,673,402 issued to Weisman, Houghton and Gellert on Jun. 16, 1987; U.S. Pat. No. 4,834,735 issued to Alemany and Berg on May 30, 1989; and U.S. Pat. No. 4,888,231 issued to Angstadt on Dec. 19, 1989 also describe absorbent structures that are useful in the present invention. Each of these references are incorporated herein by reference. The absorbent core 28 is preferably a batt of airfelt and particles of absorbent gelling material, about 13 centimeters wide (lateral dimension), about 37 centimeters long (longitudinal dimension) and approximately 8 centimeters across the narrowest part of the crotch portion 57. Preferably, the portion of the absorbent core that will be generally located in the front portion 56 and crotch portion 57 will have a higher basis weight than the portion of the absorbent core that will be generally located in the rear portion 58. More preferably, the portion of the absorbent core that will be generally located in the front portion 56 and crotch portion 57 will have a basis weight three times the basis weight of the portion of the absorbent core that will be generally located in the rear portion 58. In a preferred embodiment of the absorbent core 28, about 25.4 centimeters of the absorbent core's length will be generally located in the front portion 56 and crotch portion 57 and will have a basis weight of about 0.69 grams per square inch, and 11.4 centimeters of the absorbent core's length will be generally located in the rear portion 58 and will have a basis weight of about 0.23 grams per square inch.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waist-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werencz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably s manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the disposable training pants 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 01012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuff 32 will be free from any backsheet material, and, thus are not inhibited by the backsheet material. Alternatively, the topsheet 24 may wrap around the core and under the edge portion of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the areas extending beyond the absorbent core 28 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A suitable topsheet is manufactured by Fiberweb North America and available as 80/20 polypropylene/rayon carded thermally bonded nonwoven.

Figure 3:
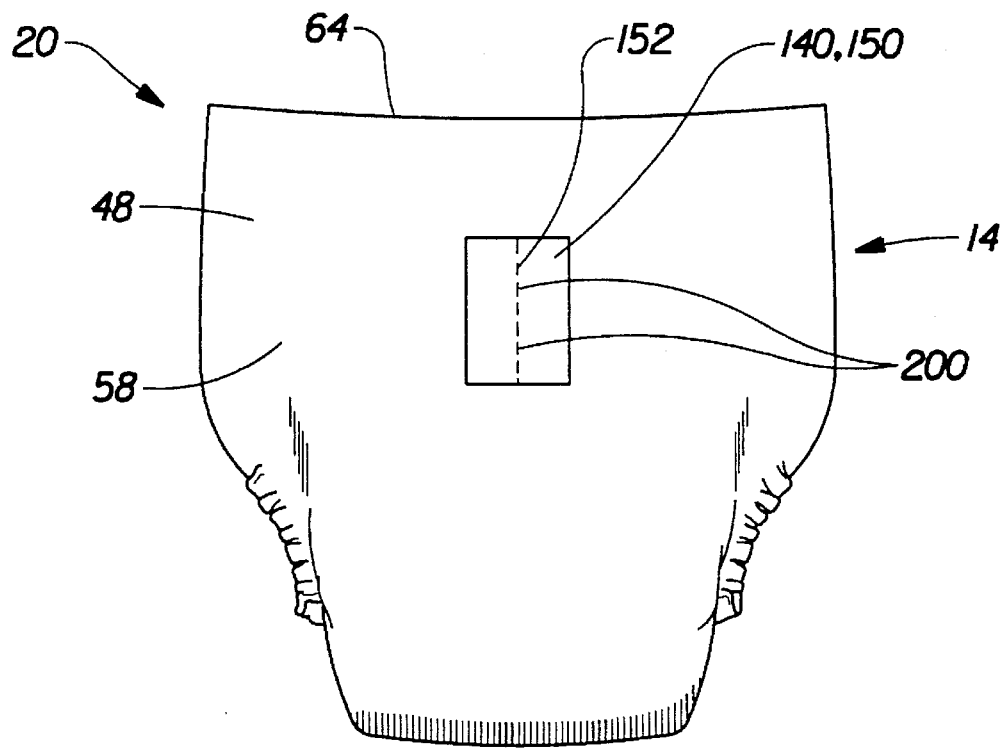
FIG. 3 is a perspective view of the disposable training pant illustrating the disposal means.

Referring now to FIGS. 1 and 3, the training pant 20 preferably comprises disposal means 140 for allowing the training pant 20 to be secured in a disposal configuration so as to provide convenient disposal of the training pant 20. Thus, the disposal means 140 may be any structure that allows the training pant 20 to be folded, or rolled up into a configuration for disposal and secured in that configuration to contain the contents within the soiled training pant. Thus, for example, the disposal means 140 may comprise a number of different elements such as adhesive tape tabs, adhesive attachment means, mechanical fastening elements, a hook fastening material, a loop fastening material, or any other element or combination of elements readily known to those of skill in the art.

The disposal means 140 may be positioned anywhere on the chassis 14 so long as it secures the training pant 20 in a configuration for disposal. For example, the disposal means 140 may be positioned on the outer layer 48 in front portion 56 or on the outer layer 48 in the rear portion 58. The disposal means 140 is shown in FIGS. 1 and 3 positioned on the outer layer 48 in the rear portion 58.

Figure 4:
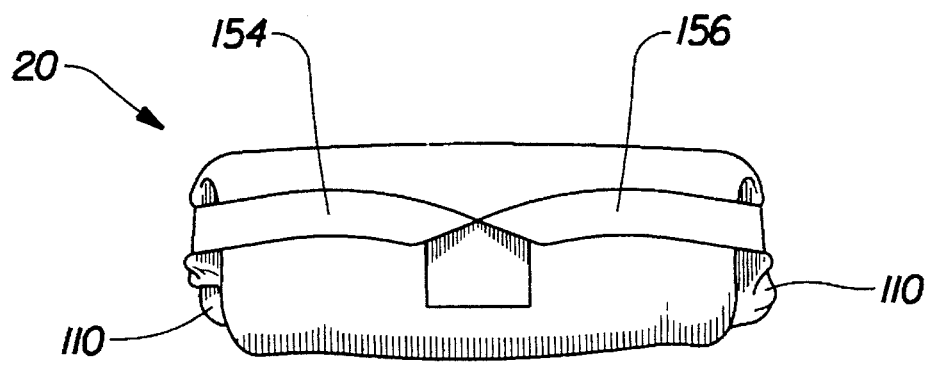
FIG. 4 is a perspective view showing the disposable training pant of FIG. 3 in its disposal configuration.

The preferred embodiment of the training pant 20 illustrated in FIG. 3 has a disposal means 140 comprising an adhesive tape tab 150 positioned on the outer layer 48 of the chassis 14. The adhesive tape tab 150 preferably comprises a frangible section 152. The frangible section 152 is constructed to provide for a separation of the tape tab 150 into generally independently movable strip portions 154 and 156, as illustrated in FIG. 4. The separability or frangibility of section 152 may be provided by any suitable treatment which reduces the strength of tape tab 150. For example, the frangibility of section 152 may be provided by selectively reducing the thickness of tape tab 150 along section 152, by providing a line of perforations 200 along the frangible section, by inducing a pattern of stress fatigue weakness along frangible section 152, or by a like arrangement.

Figure 5:
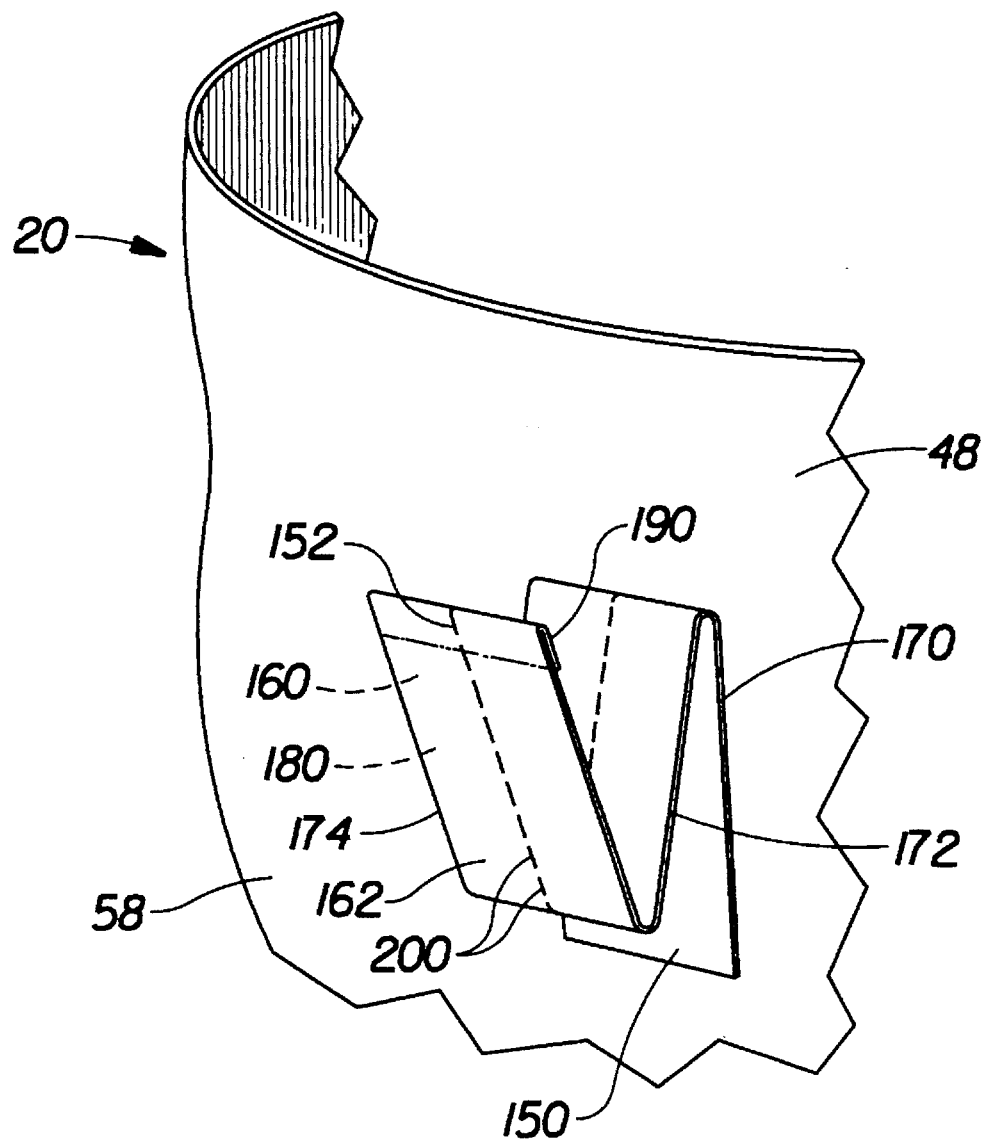
FIG. 5 is an enlarged fragmented perspective illustration of the disposable training pant illustrating the disposal means.

An enlarged illustration of the adhesive tape tab 150 is shown in FIG. 5. The adhesive tape tab 150 is shown in FIG. 5 in a partially extended configuration prior to separation along frangible section 152 to better illustrate the various components. The adhesive tape tab 150 has a fastening surface 160 and a backing surface 162. The fastening surface is that surface of the adhesive tape tab 150 designed to engage other portions of the training pant 20, such as the outer layer 48, to secure the training pant 20 into a configuration for disposal. The backing surface 162 is that surface opposed to the fastening surface 160. The backing surface is generally exposed during wear of the training pant 20. The tape tab 150 is joined to the outer layer 48 to create a fixed portion 170 (i.e., that end of tape tab 150 joined to the training pant during manufacture). The tape tab 150 has another element which forms the user's end (i.e., that joint made by the person in securing the training pant in a configuration for disposal). Thus the tape tab has at least three elements, a fixed portion 170, a first connective portion 172, and a second connective portion 174. The fixed portion 170 is that portion of the tape tab 150 which is attached to the outer layer 48. The fixed portion 170 thus forms the manufacturers end of the tape tab 150. The second connective portion 174 is that portion of the tape tab 150 which is attached to another portion of the training pant 20, by the user when securing the training pant in a configuration for disposal. The second connective portion thus forms the user's end. The first connective portion 172 serves to connect the fixed portion 170 to the second connective portion 174, and to properly orient the second connective portion 174 for disposal.

The fastening surface 160 of the second connective portion 174 includes a fastening component, such as an adhesive attachment layer or a mechanical closure element, positioned on and joined to the tape tab 150. The fastening component preferably comprises an adhesive attachment layer 180 coated on the second connective portion 174 to form the fastening surface 160.

As shown is FIG. 5, the tape tab 150 may also have a grip tab 190 at the distal edge of the second connective portion 174. The grip tab 190 may be formed by folding over a small margin of the distal edge of the second connective portion 174 and attaching it to itself. This forms an end of the second connective portion 174 which is easier to grasp.

While the tape tab 150 may be positioned anywhere on the chassis 14, the tape tab 150 is preferably disposed in the rear portion 58 away from the end edge 64 of the training pant 20 and preferably transversely centered in the rear portion 58, to provide disposal means 140. Thus, when the training pant 20 is folded or rolled up after soiling, the user separates the tape tab 150 along frangible section 152 into independent portions 154 and 156 and secures independent portions 154 and 156 to the outer layer 48 or another portion of the training pant 20 to provide secure closure of the rolled-up training pant. The independent portions 154 and 156 are preferably long enough such that they may be extended to effectively seal the leg openings 110, as shown in FIG. 4. Sealing the leg openings 110 contains the contents within the soiled training pant 20. The tape tab 150 may be comprised of stretchable or extensible material, such as natural or synthetic elastics, or composite elastic materials, to allow the independent portion 154 and 156 to extend to promote sealing of the leg openings 110.

While the tape tab 150 is shown in FIG. 3 as having one frangible section 152, the tape tab 150 may include several frangible sections 152. For example, the tape tab 150 may include two frangible sections 152 allowing the tape tab to be separated into three independent portions.

In an alternative embodiment, the first connective portion 172 is extensible, preferably in an elastic manner. The first connective portion 172 may comprise an elastomeric film or a structural elastic-like film web as disclosed in International Publication Number WO 95/03765, The Procter & Gamble Company, published Feb. 9, 1995, in the name of Chappell et al. and is incorporated herein by reference. The first connective portion 172 may comprise a different material from that of the second connective portion 174 and the first portion 170 to provide extensibility.

While particular embodiments of the present invention have been illustrated and described, it would be obvious to those skilled in the art that various other changes and modification can be made without departing from the spirit and scope of the invention. It is therefore intended to cover in the appended claims all such changes and modifications that are within the scope of this invention.

What is claimed is:

1. A disposable garment comprising:
   (a) a chassis having a front portion, a rear portion opposed to said front portion, and a crotch portion positioned between said front portion and said rear portion, said chassis comprising an outer layer and an inner layer;
   (b) seams joining said front portion to said rear portion so as to form two leg openings and a waist opening; and
   (c) disposal means joined to said outer layer for allowing the disposable garment to be secured in a configuration that provides convenient disposal of the disposable garment, said disposal means comprising a frangible section to provide for separation of said disposal means into independent portions each adapted to secure the disposable garment in a configuration for disposal.

2. The disposable garment of claim 1 wherein said disposal means comprises a fixed portion joined to said outer layer and a connective portion joined to said fixed portion, said connective portion having a fastening surface.

3. The disposable garment of claim 2 wherein said fastening surface has an adhesive disposed thereon.

4. The disposable garment of claim 2 wherein said connective portion comprises a first connective portion and a second connective portion.

5. The disposable garment of claim 4 wherein said first connective portion comprises an extensible material.

6. The disposable garment of claim 1 wherein said frangible section comprises a line of perforations.

7. The disposable garment of claim 1 wherein said disposal means comprises an extensible material.

8. The disposable garment of claim 1 wherein said disposal means is disposed in the rear portion.

9. The disposable garment of claim 1 wherein said disposal means is disposed in the front portion.

10. The disposable garment of claim 1 wherein said chassis additionally comprises an absorbent assembly secured to said inner layer.

11. The disposable garment of claim 10 wherein said absorbent assembly comprises a topsheet, a backsheet secured to said topsheet, and an absorbent core interposed between said topsheet and said backsheet, said backsheet being secured to said inner layer.

12. The disposable garment of claim 1 wherein said front portion has an end edge, longitudinal side edges, and leg edges.

13. The disposable garment of claim 1 wherein said rear portion has an end edge, longitudinal side edges, and leg edges.

* * * * *